US007553615B2

(12) United States Patent
Heindl et al.

(10) Patent No.: US 7,553,615 B2
(45) Date of Patent: Jun. 30, 2009

(54) COMPOUNDS, METHODS, COMPLEXES, APPARATUSES AND USES RELATING TO STABILE FORMS OF NAD/NADH

(75) Inventors: Dieter Heindl, Pahl (DE); Joachim Hoenes, Zwingenberg (DE); Carina Horn, Biblis (DE); Piet Herdewijn, Rotselaar (BE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 94 days.

(21) Appl. No.: 11/460,366

(22) Filed: Jul. 27, 2006

(65) Prior Publication Data

US 2007/0026476 A1 Feb. 1, 2007

(30) Foreign Application Priority Data

Jul. 28, 2005 (DE) .................. 10 2005 035 469

(51) Int. Cl.
*C12Q 1/00* (2006.01)
*C12Q 1/32* (2006.01)
*C07H 19/207* (2006.01)

(52) U.S. Cl. ........................... 435/4; 435/26; 536/26.24

(58) Field of Classification Search ...................... None
See application file for complete search history.

(56) References Cited

U.S. PATENT DOCUMENTS 5,801,006 A 9/1998 Kaufman
5,912,139 A * 6/1999 Iwata et al. .................... 435/26

FOREIGN PATENT DOCUMENTS

WO    WO 98/33936 A1    8/1998
WO    WO 01/49247 A2    7/2001
WO    WO 01/94370 A1    12/2001

OTHER PUBLICATIONS

Niekamp et al. Correlations Between Tertiary Structure and Energetics of Coenzyme Binding in Pig Heart Muscle Lactate Dehydrogenase; Biochemistry, vol. 19 (1980) pp. 3144-3152.*
Mizunari et al. Nucleoside-Triphosphate Binding of teh Two Cytosolic Components of the Respiratory Burst Oxidase System: Evidence for Its Inhibition by the 2',3'-Dialdehyde Derivative of NADPH and Desensitization in Thier Translocated States; Biochimica et Biophysica Acta, vol. 1220 (1993) pp. 21-30.*
Lark et al. Reaction of the 2',3'-Dialdehydederivative of NADPH at a Nucleotide Site of Bovine Liver Glutamate Dehydrogenase; The Journal of Biological Chemistry, vol. 261, No. 23 (1986) pp. 10659-10666.*
Jeck et al. New Reactive Coenzyme Analogues for Affinity Labeling of NAD+ and NADP+ Dependent Dehydrogenases; Zeitschrift fur Naturforschung. C, Journal of Biosciences, vol. 50, No. 7-8 (1995) pp. 476-486.*
Woenckhaus et al. Preparation and Properties of Nicotinamide-N1-Beta-Glucopyranosyl Phosphate and Nicotinamide-Glucoside-Adenine Dinucleotide; Zeitschrift fur Naturforschung, No. 19b (1964) pp. 467-470; with English translation.*
Slama, James T. and Anne M. Simmons, "Carbanicotinamide Adenine Dinucleotide: Synynthesis and Enzymological Propertied of a Carboncyclic Analogue of Oxidized Nicotinamide Adenine Dinucleotide," *Biochemistry*, vol. 27, pp. 183-193 (1988).
Kaplan, Nathan O. and Margaret M. Giotti, "Chemistry and Properties of the 3-Acetylpyridine Analogue of Diphosphopyridine Nucleotide," *Journal of Biochemistry*, pp. 823-832 (1956).
Oppenheimer, Norman J., "Chemistry and Solution Conformation of the Pyridine Coenzymes," *Academic Press*, Chapter 3, pp. 51-89 (1982).
Anderson, Bruce M., "Analogs of Pyridine Nucleotide Coenzymes," pp. 91-133.
Slama, JT and Simmons AM, "Inhibition of NAD glycohydrolase and ADP-ribosyl transferases by carbocyclic analogues of oxidized nicotinamide adenine dinucleotide," *Biochemistry*, vol. 28, No. 19, pp. 7688-7694 (Sep. 19, 1989).—Abstract from Pub Med.
Kuchen, W., Buchwald, H., Strolenberg, K. and Metten, J., "Synthesis of Dialkylphosphorus Compounds," *Institute for Inorganic Chemistry and Electrochemistry of the Technische Hochschule Aachem*, Nov. 8, 1961.
Andersen, Marc W., Daluge, Susan M. Kerremans, Luk and Herdewijn, Piet, The Synthesis of Modified D- and L-Anhydrohexitol Nucleosides, *Tetrahedron Letters*, vol. 37, No. 45, pp. 8147-8150.
Wang, Jing, Morral, Jordi, Hendrix, Chris and Piet Herdewijn, "A Straightforward Stereoslective Sysnthesis of D- and L-5-Hydroxy-4-hydroxymethyl-2-cyclohexenylguanine," *Journal of Organic Chemistry*, vol. 66, No. 25, pp. 8478-8482 (2001).
Furusawa, Kiyotaka, Sekine, Mitsuo and Hata, Tsujiaki, "Studies on Phosphastes. Part III. A New method for the Synthesis of Nucleotide Coenzymes by Means of Di-n-butylphosphinothioyl Bromide," pp. 1711-1716 (Feb. 4, 1976).
Gu, Ping, Griebel, Carsten, Van Aerschot, Arthur, Rozenski, Jef, Busson, Roger, Gais, Hans-Joachim and Herdewijn Piet, "Synthesis of enantiomeric-pure cyclohexenyl nucleoside building blocks for oligonucleotide synthesis," *Tetrahedron 60*, pp. 2111-2123 (2004).
Allart, Brigitte, Busson, Roger, Rozenski, Jef, Van-Aerschot, Arthur and Herdewijn, Piet, "Synthesis or Protected D-Altritol Nucleosides as Building Blocks for Oligonucleotide Synthesis," *Tetrahedron 55*, pp. 6527-6546 (1999).
Hutchinson, Edward J., Taylor, Brian F. and Blackburn, G. Michael, "Synthesis of carbocyclic $NAD^+$ contaiing a methylenebisphosponate linkage for the investigation of ADP-ribosyl cyclase," *Chem. Commun.*, pp. 2765-2766 (1996).
Slama, James T., Radziejewski, Czestaw, Oruganti, RubbaRao and Kaiser, E. T., "Semisynthetic Enzymes: Characterization of Isomeric Flavopapains with Widely Different Catalytic Efficiencies," *Journal of American Chemistry Society*, vol. 106, pp. 6778-6785 (1984).

* cited by examiner

*Primary Examiner*—Jon P Weber
*Assistant Examiner*—Paul C. Martin
(74) *Attorney, Agent, or Firm*—Justin L. Sage; Roche Diagnostics Operations, Inc.

(57) ABSTRACT

The invention concerns stable nicotinamide adenine dinucleotide (NAD/NADH) and nicotinamide adenine dinucleotide phosphate (NADP/NADPH) derivatives, enzyme complexes of these derivatives and their use in biochemical detection methods and reagent matrices.

11 Claims, 3 Drawing Sheets

COMPOUNDS, METHODS, COMPLEXES, APPARATUSES AND USES RELATING TO STABILE FORMS OF NAD/NADH

REFERENCE TO RELATED APPLICATIONS

The present application is based on and claims priority to German Patent Application No. 10 2005 035 469.6, filed Jul. 28, 2005, which is hereby incorporated by reference in its entirety.

TECHNICAL FIELD

The invention concerns stable nicotinamide adenine dinucleotide (NAD/NADH) and nicotinamide adenine dinucleotide phosphate (NADP/NADPH) derivatives, enzyme complexes of these derivatives and their use in biochemical detection methods and reagent matrices.

BACKGROUND

Measuring systems for biochemical analytics are important components of clinically relevant analytical methods. This primarily concerns the measurement of analytes e.g. metabolites or substances which are determined directly or indirectly with the aid of an enzyme. The analytes are converted with the aid of an enzyme-coenzyme complex and subsequently quantified. In this process the analyte to be determined is contacted with a suitable enzyme and a coenzyme where the enzyme is usually used in catalytic amounts. The coenzyme is changed e.g. oxidized or reduced by the enzymatic reaction. This process can be detected electrochemically or photometrically either directly or by means of a mediator. A calibration yields a direct correlation between the measured value and the concentration of the analyte to be determined.

Coenzymes are organic molecules which are covalently or non-covalently bound to an enzyme and are changed by the conversion of the analyte. Prominent examples of coenzymes are nicotinamide adenine dinucleotide (NAD) and nicotinamide adenine dinucleotide phosphate (NADP) from which NADH or NADPH respectively are formed by reduction.

Measuring systems known from the prior art are characterized by a limited shelf-life and by special requirements for the environment such as cooling or dry storage in order to achieve this storage stability. Hence erroneous results caused by incorrect, unnoticed, faulty storage can occur for certain forms of application, e.g. in the cases of tests which are carried out by the end-users themselves such as blood glucose self-monitoring. Especially the exhaustion of desiccants due to opening the primary packaging for excessive periods can result in measuring errors which in some systems can be hardly recognized by the consumer.

A known measure that can be used to increase the stability of biochemical measuring systems is the use of stable enzymes, e.g. the use of enzymes from thermophilic organisms. It is also possible to stabilize enzymes by chemical modification, e.g. cross-linking or by mutagenesis. Furthermore, enzyme stabilizers such as trehalose, polyvinylpyrrolidone and serum albumin can also be added or the enzymes can be enclosed in polymer networks, e.g. by photopolymerization.

It has also been attempted to improve the storage life of biochemical measuring systems by using stable mediators. Thus the specificity of tests is increased and interferences during the reaction are eliminated by using mediators having the lowest possible redox potential. However, the redox potentials of the enzyme/coenzyme complexes constitutes a lower limit for the redox potential. If those fall below this limit, the reaction with the mediators is slowed down or even prevented.

Alternatively it is also possible to use biochemical measuring systems without mediators in which for example coenzymes such as the coenzyme NADH are directly detected. However, a disadvantage of such measuring systems is that coenzymes such as NAD and NADP are unstable.

NAD and NADP are base-labile molecules, the degradation paths of which are described in the literature (N. J. Oppenheimer in The Pyridine Nucleotide Coenzymes Academic Press, New York, London, 1982, J. Everese, B. Anderson, K. You, Editors, chapter 3, pages 56-65). Essentially ADP-ribose is formed during the degradation of NAD or NADP by cleavage of the glycosyl bonds between the ribose and the pyridine unit. The reduced forms NADH and NADPH are, however, acid labile. For example, epimerization is a known degradation path. In both cases, the instability of NAD/NADP and NADH/NADPH is due to the lability of the glycosyl bonds between the ribose and the pyridine unit. But even under less drastic conditions such as in aqueous solution, the coenzymes NAD or NADP are already hydrolyzed solely by the ambient humidity. This instability can result in inaccuracies when measuring analytes.

A number of NAD/NADP derivatives are described for example in B. M. Anderson in the Pyridine Nucleotide Coenzymes, Academic Press New York, London 1982, J. Everese, B. Anderson, K. You, Editors, Chapter 4. However, most of these derivatives are not accepted well by enzymes. The only derivative which has therefore been previously used for diagnostic tests is 3-acetylpyridine adenine dinucleotide (acetyl NAD) which was first described in 1956 (N. O. Kaplan, *J. Biol. Chem.* (1956) 221, 823). This coenzyme is also not accepted well by enzymes and exhibits a change in the redox potential.

The use of other NAD derivatives with a modified pyridine group is described in WO 01/94370. However, modifications of the nicotinamide group usually have a direct effect on the catalytic reaction. In most cases this effect is negative.

In another stabilization concept the ribose unit was modified in order to influence the stability of the glycosyl bond. This process does not directly interfere with the catalytic reaction of the nicotinamide group. However, there may be an indirect effect as soon as the enzyme binds strongly and specifically to the ribose unit. In this connection Kaufmann et al. disclose a number of thioribose-NAD derivatives in WO 98/33936 and U.S. Pat. No. 5,801,006 and WO 01/49247. However, a correlation between the modification of the nicotinamide ribose unit and the activity of the derivatives in enzymatic reactions has previously not been demonstrated.

CarbaNAD, a derivative without a glycosyl bond was described for the first time in 1988 (J. T. Slama, Biochemistry 1989, 27, 183 and Biochemistry 1989, 28, 7688). In this derivative the ribose is substituted by a carbacyclic sugar unit. Although carbaNAD was described as a substrate for dehydrogenases, its activity has not yet been proven in clinical biochemical detection methods.

A similar approach was described later by G. M. Blackburn, *Chem. Comm.*, 1996, 2765 in order to synthesize carbaNAD with a methylene bisphosphonate compound instead of the natural pyrophosphate. The methylene bisphosphonate is more stable towards phosphatases and was used as an inhibitor for a ADP ribosylcyclase. The aim was not to make it more resistant to hydrolysis (J. T. Slama, G. M. Blackburn).

Hence the object of the present invention is to provide stable bioanalytical measuring systems especially for determining glucose which avoid the sensitivity to hydrolysis of NAD/NADP and at the same time are active as coenzymes in enzyme reactions.

SUMMARY

This object is achieved by a test element for determining an analyte comprising (i) a coenzyme-dependent enzyme or a substrate for such an enzyme and (ii) a compound of the following general formula (I), or a salt or optionally a reduced form thereof, as the coenzyme:

(I)

in which
- A=adenine or an analog thereof;
- T=O or S;
- U=OH, SH, $BH_3^-$, or $BCNH_2^-$;
- V=OH or a phosphate group;
- W=COOR, $CON(R)_2$, COR, or $CSN(R)_2$, in which R denotes H or $C_1$-$C_2$ alkyl;
- X1, X2=O, $CH_2$, $CHCH_3$, $C(CH_3)_2$, NH, or $NCH_3$;
- Y=NH, S, O, or $CH_2$;
- Z=(i) a linear group containing 4-6 C atoms, for example 4 C atoms in which 1 or 2 C atoms are optionally replaced by one or more heteroatoms selected from O, S and N; or
  - (ii) a group comprising a cyclic compound containing 6 C atoms which optionally contains one or more heteroatoms selected from O, S and N and optionally one or more substituents, and a residue $C(R4)_2$ bound to the cyclic compound and to X2;
  - where R4 denotes H, F, or $CH_3$;
- provided that Z and the pyridine residue are not linked by a glycosidic bond.

In one embodiment, W=$CONH_2$ or $COCH_3$.

Substituents on Z in another embodiment are selected from the group comprising OH, F, Cl, and $C_1$-$C_2$ alkyl which are optionally fluorinated or chlorinated and/or OH-substituted, O—$C_1$-$C_2$ alkyl.

In another embodiment, a test element is used to determine glucose which comprises a glucose dehydrogenase and a compound of the general formula (I) as mentioned above or a salt thereof.

Surprisingly, the compounds according to the invention are stable towards hydrolysis and are good substrates in enzymatic detection methods and can be used for biochemical diagnostics. This finding is in contrast to that of most of the previously known NAD/NADP derivatives since these derivatives are usually stable for only very short periods in enzymatic detection methods.

Some observations of the compounds according to the invention compared to the prior art are:
- higher stability,
- higher enzymatic activity,
- simpler and more efficient synthesis,
- they can be used in all previously known biochemical detection methods.

Some problems of the previously known biochemical detection methods can be largely avoided by the provision of stable NAD/NADP derivatives using the present invention, for example in combination with a stabilizing formulation such as, for example, by enclosing enzymes in polymer networks. Moreover, it is not necessary to use stabilizing additives. This is particularly advantageous since the lower the number of reactive substances involved, the greater is the chance of obtaining a stable formulation for the analyte determination.

The present invention provides tests elements comprising a number of stable NAD/NADP derivatives which have an adequate enzymatic activity for use as a coenzyme on the test element.

Stable NAD/NADP derivatives can be produced in generally known processes of synthesis. For this, the amino group of a cyclic amino alcohol is converted into a pyridinium derivative by Zincke chemistry. The primary OH group is subsequently phosphorylated and coupled to an activated AMP derivative to form an NAD derivative. Alternatively, the primary OH group can also be firstly phosphorylated and then the amino group can be converted into a pyridine by means of the Zincke reaction.

Another synthetic route is to activate the primary alcohol to form a tosylate or iodide and subsequently alkylate ADP.

Other embodiments of a test element according to the invention comprise, for example, compounds having the following general formula (I'), or a salt or optionally a reduced form thereof:

(I')

in which
- A=adenine or an analog thereof;
- T=O or S;
- U=OH, SH, $BH_3^-$, or $BCNH_2^-$;
- V=OH or a phosphate group;
- W=COOR, $CON(R)_2$, COR, or $CSN(R)_2$, in which R denotes H or $C_1$-$C_2$ alkyl;
- X1,X2=O, $CH_2$, $CHCH_3$, $C(CH_3)_2$, NH, or $NCH_3$;
- Y=NH, S, O, or $CH_2$;
- Z=a saturated or unsaturated carbocyclic or heterocyclic six-membered ring, such as a compound having the general formula (II):

(II)

in which a single or double bond can in each case independently be present between R1 and R2 or between R1' and R2', wherein if a single bond is present between R1 and R2 or R1' or R2' respectively:
R1, R1'=O, S, NCH$_3$, NH, C(R4)$_2$, CHOH, or CHOCH$_3$, where R1 and R1' cannot at the same time be a heteroatom, and
R2, R2'=C(R4)$_2$, CHOH, or CHOCH$_3$;
and wherein if a double bond is present between R1 and R2 or R1' and R2' respectively:
R1, R1', R2, R2'=CR4, and
R4=H, F, Cl, or CH$_3$; and
R6, R6'=CH or CCH$_3$.

Compounds of the following formula (I″), or a salt or optionally a reduced form thereof, are another subject matter of the invention:

(I″)

in which
A=adenine or an analog thereof;
T=O or S;
U=OH, SH, BH$_3^-$, or BCNH$_2^-$;
V=OH or a phosphate group;
W=COOR, CON(R)$_2$, COR, or CSN(R)$_2$, in which R=H or C$_1$-C$_2$ alkyl;
X1, X2=O, CH$_2$, CHCH$_3$, C(CH$_3$)$_2$, NH, or NCH$_3$;
Y=NH, S, O, or CH$_2$;
Z=(i) a linear group of the general formula —(C(R4)$_2$)$_n$— in which
n=4-6, and
R4=H, F, Cl, CH$_3$, or CH$_2$OH
provided that at least one residue U is BH$_3^-$ or BCNH$_2^-$;
or (ii) a saturated or unsaturated carbocyclic or heterocyclic six-membered ring, such as a compound of the general formula (II)

(II)

in which a single or double bond can in each case independently be present between R1 and R2 or between R1' and R2', wherein if a single bond is present between R1 and R2 or R1' and R2' respectively:
R1, R1'=O, S, NCH$_3$, NH, C(R4)$_2$, CHOH, or CHOCH$_3$, where R1 and R1' cannot at the same time be a heteroatom, and
R2, R2'=C(R4)$_2$, CHOH, or CHOCH$_3$;
and wherein if a double bond is present between R1 and R2 or R1' and R2' respectively:
R1, R1', R2, R2'=CR4, and
R4=H, F, Cl, or CH$_3$; and
R6, R6'=CH or CCH$_3$.
provided that Z and the pyridine residue are not linked by a glycosidic bond.

In one embodiment, the compounds according to the invention contain adenine analogs such as C$_8$-substituted and N$_6$-substituted adenine, deaza variants such as 7-deaza, aza variants such as 8-aza or combinations such as 7-deaza or 8-aza or carbocyclic analogs such as formycin where the 7-deaza variants can be substituted in the 7 position with halogen, C$_1$-C$_6$ alkinyl, C$_1$-C$_6$ alkenyl or C$_1$-C$_6$ alkyl.

In another embodiment, the compounds contain adenosine analogs which contain for example 2-methoxydeoxyribose, 2'-fluorodeoxyribose, hexitol, altritol or polycyclic analogues such as bicyclic, LNA and tricyclic sugars instead of ribose.

In particular, (di)phosphate oxygens can also be isoelectronically substituted such as for example O$^-$ by S$^-$ or BH$_3^-$, O by NH, NCH$_3$ or CH$_2$ and =O by =S.

Another preferred embodiment is a compound and a test element comprising the same having the general formula (III), or a salt or optionally a reduced form thereof:

(III)

in which
U=OH, SH, BH$_3^-$, or BCNH$_2^-$;
V=OH or a phosphate group;
W=COOR, CON(R)$_2$, COR, or CSN(R)$_2$, where R=H or C$_1$-C$_2$ alkyl;
X=O, CH$_2$, or NH;
R1=C(R4)$_2$, O, S, NCH$_3$, NH, CH, CHOH, or CHOH$_3$, wherein R4=H, F, Cl, or CH$_3$; and
R4'=H or OH.

Biochemical tests for analytes, for example parameters in body fluids such as blood, serum, plasma or urine or in samples of waste water or of foods are of major importance in diagnostics. In theses tests the analyte to be determined is brought into contact with a suitable enzyme and a coenzyme.

Hence, another subject matter of the present invention is an enzyme-coenzyme complex consisting of a compound according to the invention in combination with a suitable enzyme.

Any biological or chemical substances that can be detected by a redox reaction can be determined as analytes, e.g. substances which are substrates of coenzyme-dependent enzyme or the coenzyme-dependent enzymes themselves. Examples of analytes are glucose, lactic acid, malic acid, glycerol, alcohol, cholesterol, triglycerides, ascorbic acid, cysteine, glutathione, peptides, urea, ammonia, salicylate, pyruvate, 5'-nucleotidase, creatine kinase (CK), lactate dehydrogenase (LDH), carbon dioxide, etc.

For the detection of enzyme substrates, the test element can contain an enzyme that is suitable for detecting the substrate, in addition to the coenzyme. Suitable enzymes are for example dehydrogenases selected from glucose dehydrogenase (E.C.1.1.1.47), lactate dehydrogenase (E.C.1.1.1.27, 1.1.1.28), malate dehydrogenase (E.C.1.1.1.37), glyceral dehydrogenase (E.C.1.1.1.6), alcohol dehydrogenase (E.C.1.1.1.1.1), alpha-hydroxybutyrate dehydrogenase, sorbitol dehydrogenase or amino acid dehydrogenase e.g. L-amino acid dehydrogenase (E.C.1.4.1.5). Further suitable enzymes are oxidases such as glucose oxidase (E.C.1.1.3.4) or cholesterol oxidase (E.C.1.1.3.6) or aminotransferases such as aspartate or alanine aminotransferase, 5'-nucleotidase or creatine kinase.

For the detection of enzymes, the test element can contain an enzyme substrate suitable for detecting the enzyme, in addition to the coenzyme.

Another subject matter of the present invention is the use of a compound according to the invention or an enzyme-coenzyme complex according to the invention to detect an analyte in a sample by an enzymatic reaction. In this connection the detection of glucose with the aid of glucose dehydrogenase is particularly preferred.

The change in the coenzyme, i.e. in the compound according to the invention, by reaction with the analyte (if the analyte is an enzyme substrate) or by an analyte-catalysed reaction (if the analyte is an enzyme), can in principle be detected in any desired manner. Basically all methods for detecting enzymatic reactions that are known from the prior art can be used, for example optical methods and electrochemical methods. However, for purposes of illustrating the following description, the method to detect the change in the coenzyme is stated to be by optical methods. Examples of optical detection methods include the measurement of absorption, fluorescence, circular dichroism (CD), optical rotary dispersion (ORD), refractometry, etc. Fluorescence measurement, for example, is highly sensitive and enables the detection even of low concentrations of the analyte in miniaturized systems.

A liquid test can be used to detect an analyte i which the reagent is present, for example, in the form of a solution of suspension in an aqueous or non-aqueous liquid or it is present as a powder or lyophilisate. It is, however, also possible to use a dry test, in which case the reagent is applied to a carrier. The carrier can, for example, be a test strip comprising an absorbent or/and swellable material that is wetted by the sample liquid to be examined.

A gel matrix in which an enzyme-coenzyme complex is incorporated can, however, also be used as a detection reagent (cf. DE 102 218 45 A1).

In this case, the enzyme can either be polymerized into the matrix together with the compound according to the invention or, after the polymerization, the matrix can be contacted with a solution of the coenzyme in the presence of the enzyme to form the corresponding enzyme-coenzyme complex.

Another subject matter of the present invention concerns a reagent matrix and its use to detect analytes. The reagent matrix can contain a compound according to the invention, a suitable enzyme and a suitable reaction buffer. Suitable enzymes have already been described. The reagent matrix according to the invention can be used in a wide variety of ways and can be used to determine analytes such as glucose, lactic acid, malic acid, glycerol, alcohol, cholesterol, triglycerides, ascorbic acid, cysteine, glutathione, peptides, urea, ammonia, salicylate, pyruvate, 5'-nucleotidase, CK, LDH, carbon dioxide, etc.. A reagent matrix in one embodiment contains a compound according to the invention and glucose dehydrogenase (E.C.1.1.1.47) to detect glucose in blood.

The reagent matrix according to the invention can be used to detect an analyte in a dry or liquid test.

Another subject matter of the present invention concerns a test strip for the fluorometric or photometric detection of an analyte. Such a test strip contains a compound as stated above as a coenzyme and optionally a suitable enzyme or an enzyme substrate immobilized on an absorbent or/and swellable material. Suitable materials can for example be selected from cellulose, plastics etc.

Another subject matter of the present invention comprises a method for detecting an analyte comprising the steps:
(a) contacting a sample with a test element or reagent matrix according to the invention comprising a coenzyme and
(b) detecting the analyte e.g. on the basis of the change in the coenzyme.

Another aspect of the invention is that the fluorescence emission of the coenzymes exhibits a bathochromic shift such that there is less interference with the fluorescence emission of other materials of the test element or/and of the sample.

Embodiments of the subject matter of the present invention that are shown are also intended to apply to other subject matters of the invention such as, e.g. other embodiments of the compounds according to the invention.

These and other features and advantages of the present invention will be more fully understood from the following detailed description of the invention taken together with the accompanying claims. It is noted that the scope of the claims is definitely by the recitations therein and not by the specific discussion of the features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment(s) of the present invention.

In order that the invention may be more readily understood, reference is made to the following examples, which are intended to illustrate the invention, but not limit the scope thereof.

DETAILED DESCRIPTION

The following descriptions of embodiments are merely exemplary in nature and are in no way intended to limit the invention or its application or uses.

The preparation of stable NAD/NADH derivatives for purposes of the present invention is shown on the basis of the synthesis schemes 1, 2 and 3 as examples (FIGS. 1, 2 and 3) described below.

All solvents were distilled before use and purified by standard methods. $^1$H NMR was measured on a 200 MHz or 500 MHz Varian instrument using TMS as an internal standard for $^1$H NMR and DMSOd$_6$ (39.6 ppm) as an internal standard for $^{13}$C NMR. $^{31}$P NMR spectra were measured using 85% $H_3PO_4$ as an external standard. Mass spectroscopy: Q-T of 2, microscale with an ESI interface.

TLC: coated aluminium strips (Fluka silica gel/TLC cards, 254 nm). Detection: UV and anisaldehyde sulphuric acid spray; column chromatography: silica gel (0.060-0.200 nm).

Synthesis Scheme 1

Figure 1:
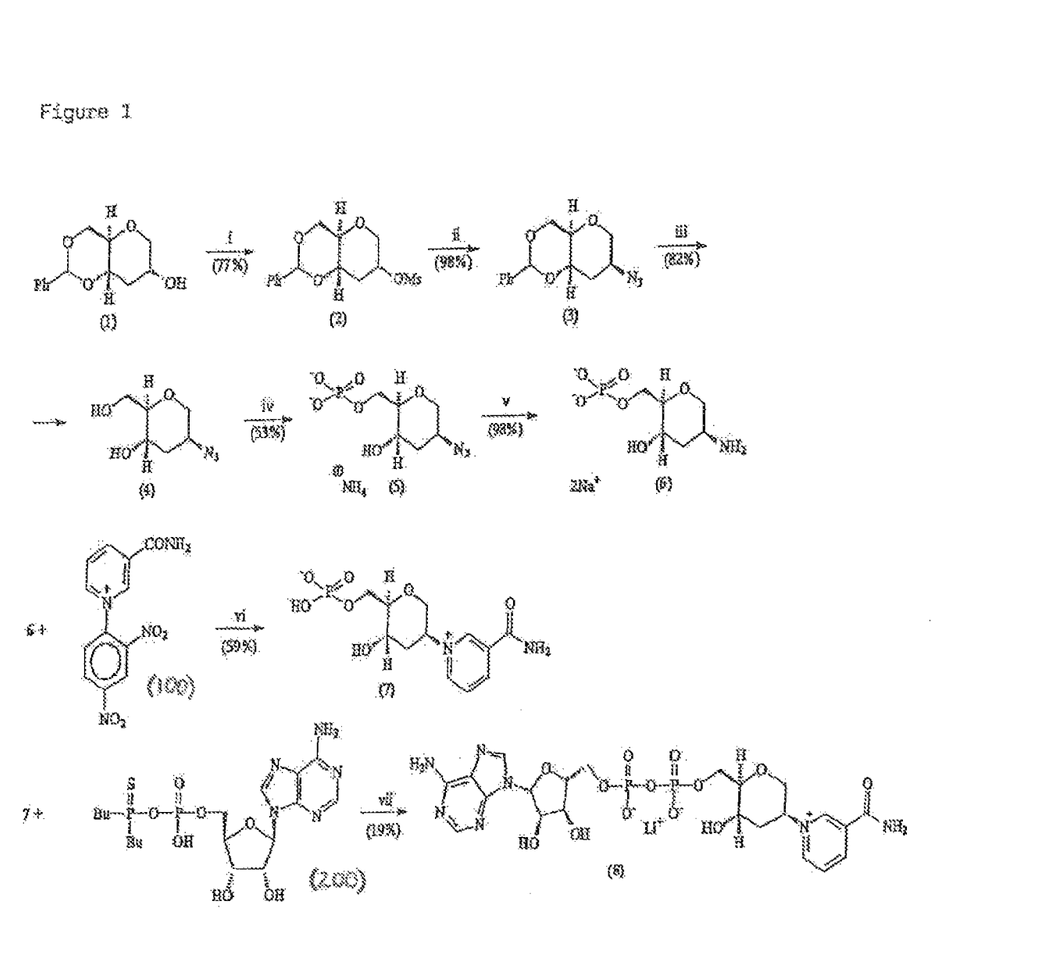
FIG. 1 is a scheme for the preparation of hexitol nicotinamide adenine dinucleotide, lithium salt.

Referring now to FIG. 1, an illustrative synthesis scheme is provided for preparation of hexitol nicotinamide adenine dinucleotide lithium salt 8 in a series of steps in which numbers refer to like-numbered molecular diagrams in FIG. 1.

Step 1: Preparation of 1,5-Anhydro-4,6-O-benzylidene-3-deoxy-2-O-methane sulfonyl-D-ribohexitol 2:

A spatula tip full of 4-dimethylaminopyridine in 40 ml absolute pyridine methane-sulfonylchloride (3 ml, 38 mmol) is added to a solution of 1,5-anhydro-4,6-O-benzylidine-3-deoxy-d-glucitol 1 (Andersen M. W. et al., *Tetrahedron Lett.*, 1996, 37, 8147-8150) (5.000 g, 21.16 mmol) while cooling on ice and stirring. The mixture is stirred at room temperature for 14 h. After evaporation using a rotary evaporator, it is stirred in toluene and again evaporated. The residue is digested three times with warm $CHCl_3$. The combined extracts are filtered over a short silica gel column. The solvent is removed on a rotary evaporator under vacuum. The residue is washed with ether and precipitated from methanol.

Yield 2: (5.103 g, 77%), $R_f$ 0.8 (hexane/EtOAc 1/2), 0.5 (hexane/EtOAc 2/1). $^1$H NMR (200 MHz, $CDCl_3$), δ 1.92 (ddd, $^2J_{3ax,3eq}$=12 Hz, $^3J_{3ax,4}$=11 Hz, $^3J_{2,3ax}$=11.5 Hz, 1H, H-3ax), 2.68 (dm, $^2J_{3ax,3eq}$=12 Hz, $^3J_{2,3eq}$=5.5 Hz, $^3J_{eq,4}$=4 Hz, 1H, H-3eq), 3.06 (s, 3H, $CH_3$), 3.32 (ddd, $^3J_{5,6ax}$=10 Hz, $^3J_{4,5}$=8 Hz, $^3J_{5,6aq}$=5 Hz, 1H, H-5), 3.41 (t, $^2J_{1ax,1eq}$=$^3J_{1ax,2}$=11 Hz, H-1ax), 3.59 (ddd, $^3J_{3ax,4}$=11 Hz, $^3J_{4,5}$=8 Hz, $^3J_{3eq,4}$=4 Hz, 1H,H-4), 3.68 (t, $^2J_{6ax,6eq}$=$^3J_{5,6ax}$=10 Hz, 1H, H-6ax), 4.21 (ddd, $^2J_{1ax,1eq}$11 Hz, $^3J_{1eq,2}$=5.5 Hz, $^4J_{1eq,3eq}$=2 Hz, 1H, H-1eq), 4.33 (dd, $^2J_{6ax,6eq}$=10 Hz, $^3J_{5,6eq}$=5 Hz, 1H, H-6eq), 4.81 (m, $^3J_{2,3ax}$=11.5 Hz, $^3J_{1ax,2}$=11 Hz, $^3J_{1eq,2}$=$^3J_{2,3eq}$=5.5 Hz, 1H, H-2), 5.53 (s, 1H, PhCH), 7.33-7.51 ppm (m, 5H, aromatic H).

Step 2: Preparation of 1,5-Anhydro-2-azido-4,6-O-benzylidene-2,3-dideoxy-D-arabino-hexitol 3:

Sodium azide (2.1 g, 32 mmol) is added to a solution of 2 (5.000 g, 15.91 mmol) in 120 ml, N,N-dimethylformamide. The mixture is heated to 80° C. for 31 h under nitrogen while stirring. After cooling to room temperature, the solvent is removed by distillation under vacuum on a rotary evaporator. The residue is digested three times with warm $CHCl_3$. The combined extracts are filtered over a short silica gel column. The solvent is removed on a rotary evaporator under vacuum. The residue is washed with ether and precipitated from hexane.

Yield 3 (4.073 g, 98%) colourless powder, $R_f$ 0.9 (hexane/EtOAc 2/1). $^1$H NMR (200 MHz, $CDCl_3$) δ 1.91 (dd, $^2J_{3ax,3eq}$=13 Hz, $^3J_{3ax,4}$=12 Hz, $^3J_{2,3ax}$=4 Hz, 1H, H-3ax), 2.33 (dm, $^2J_{3ax,3eq}$=13 Hz, 1H, H-3eq), 3.39 (ddd, $^3J_{5,6ax}$=10 Hz, $^3J_{5,6eq}$=5 Hz, 1H, H-5), 3.69 (dd, $^2J_{1ax,1eq}$=12 Hz, $^3J_{1ax,2}$=2 Hz, 1H, H-1ax), 3.77 (t, $^2J_{6ax,6eq}$=$^3J_{5,6ax}$=10 Hz, 1H, H-6ax), 3.55-4.06 (m, 3H, H-1eq, H-2, H-4), 4.28 (dd, $^2J_{6ax,6ax}$=10 Hz, $^3J_{5,6eq}$=5 Hz, 1H, H-6eq), 5.60 (s, 1H, PhCH), 7.34-7.52 ppm (m, 5H, aromatic H).

Step 3: Preparation of 1,5-Anhydro-2-azido-2,3-dideoxy-D-arabino-hexitol 4:

A solution of 3 (4.000 g, 15.31 mmol) in 180 ml 80% glacial acetic acid is stirred for 1 h at 95° C. After evaporation of a rotary evaporator it is stirred in water and again evaporated. Then it is stirred with toluene and again evaporated. The residue is purified by column chromatography (0-10% EtOAc in hexane). The solvent is removed from the combined product fraction by distillation on a rotary evaporator under vacuum. The residue is dried in a vacuum over $P_2O_3$.

Yield 4 (2.174 g, 82%) oil. $R_f$ 0.25 (hexane/EtOAc 1/2). $^1$H NMR (200 MHz, $CDCl_3$) δ 1.72 (ddd, $^2J_{3ax,3eq}$=14 Hz, $^3J_{3ax,4}$=11 Hz, $^3J_{2,3ax}$=4 Hz, 1H, H-3ax), 2.33 (dm, $^2J_{3ax,3ex}$=14 Hz, 1H, H-3eq), 2.67 (br.s, 1H, OH), 3.05 (br.s, 1H, OH), 3.20 (dm, $^3J_{4,5}$=9 Hz, 1H, H-5), 3.59 (dd, $^2J_{1ax,1eq}$=12 Hz, $^3J_{1ax,2}$=2 Hz, 1H, H-1ax), 3.74-4.04 (m, 5H, H-1eq, H-2, H-4, H-6a, H-6b).

Step 4: Preparation of 1,5-Anhydro-2-azido-2,3-dideoxy-6-O-phospono-D-arabino-hexitol ammonium salt 5:

The azide 4 (1.004 g, 5.80 mmol) is dissolved by stirring in 6 ml trimethylphosphate (freshly vacuum distilled over BaO) under nitrogen. 1.7 ml of 1/1 (v/v) mixture of phosphoryl chloride (freshly distilled) and trimethyl phosphate is added all at once at 0° C. After stirring for 3 h at 0° C., 6 ml ice water and 9 ml cold triethylamine are added. The mixture is evaporated to dryness on a rotary evaporator in a vacuum. The residue is washed with diisopropyl either and purified by column chromatography [0-35% ammonium hydroxide (20% solution in water) in i-PrOH]. The solvent is removed from the combined product fractions by distillation under vacuum on a rotary evaporator.

Yield 5 (0.677 g, 43%) pale yellow oil. Rf 0.35 (i-PrOH/25% $NH_4OH_{aq}/H_2O$ 6/3/1). $^1$H NMR (200 MHz, $D_2O$) δ 1.80 (ddd, $^2J_{3ax,3eq}$=13.5 Hz, $^3J_{3ax,4}$=11 Hz, $^3J_{2,3ax}$=3.5 Hz, 1H, H-3ax), 2.34 (dm, $^2J_{3ax,3eq}$=13.5 Hz, 1H, H-3eq), 3.43 (ddd, $^3J_{4,5}$=8.5 Hz, $^3J_{5,6a}$=5.5 Hz, $^3J_{5,6b}$=2 Hz, 1H, H-5), 3.68 (dd, $^2J_{1ax,1eq}$=12.5 Hz, $^3J_{1ax,2}$=1.5 Hz, 1H, H-1ax), 3.77-4.24 ppm (m, 5H, H-1eq, H-2, H-4, H-6a, H6b).

Step 5: Preparation of 2-Amino-1,5-anhydro-2,3-dideoxy-6-O-phosphone-D-arabino-hexitol sodium salt 6:

25 ml methanol and Adam's catalyst ($PtO_2 \cdot H_2O$, 0.068 g, 0.28 mmol) are added to a solution of the azide 5 (0.677 g, 2.51 mmol) dissolved in 75 ml water. The mixture is shaken for 2 h in a Parr hydrogenation apparatus (30 psi). The catalyst is removed by filtration and the solvent is removed from the filtrate by distillation on a rotary evaporator under vacuum. The residue is dissolved in water and applied to a Dowex 50WX4-400 ($Na^+$) ion exchange column and eluted with water. The solvent is removed from the combined product fractions by distillation on a rotary evaporator under vacuum. The residue is dried in a vacuum over $P_2O_5$.

Yield 6 (0.666 g, 98%) pale yellow solidified oil. $R_f$ 0.2 (i-PrOH/25% $-NH_4OH_{aq}/H_2O$ 6/3/1). $^1$H NMR (500 MHz, $D_2O$) δ 1.93 (ddd, $^2J_{3ax,3eq}$=14.4 Hz, $^3J_{3ax,4}$=12.1 Hz, $^3J_{2,3ax}$=4.1 Hz, 1H, H-3ax), 2.34 (m, $^2J_{3ax,3eq}$14.4 Hz, $^3J_{2,3eq}$=2.6 Hz, $^3J_{3,eq,4}$=5.1 Hz, $^4J_{1eq,3eq}$=2.6 Hz, 1H, H-3eq), 3.41 (m, $^3J_{4,5}$=9.6 Hz, $^3J_{5,6a}$=4.1 Hz, $^3J_{5,6b}$=2.2 Hz, $^4J_{5,P}$=0.5 Hz, 1H, H-5), 3.73 (m, $^3J_{2,3ax}$=4.1 Hz, $^3J_{2,3eq}$2.6 Hz, $^3J_{1ax,2}$=2.0, $^3J_{1eq,2}$=1.7 Hz, 1H, H-2), 3.78 (dd, $^2J_{1ax,1eq}$=13.2 Hz, $^3J_{1ax,2}$=2.0 Hz, 1H, H-1ax), 3.97 (ddd, $^2J_{1ax,1eq}$=13.2 Hz, $^3J_{1eq,2}$=1.7 Hz, $^4J_{1eq,3eq}$=2.6 Hz, 1H, H-1eq), 3.98 (ddd, $^3J_{3ax,4}$=12.1 Hz, $^3J_{4,5}$=9.6 Hz, $^3J_{3eq,4}$=5.1 Hz, 1H, H-4), 4.01

(ddd, $^2J_{6a,6b}$=11.8 Hz, $^3J_{5,6b}$=2.2 Hz, $^3J_{6b,P}$5.4 Hz, 1H, H-6b), 4.05 (ddd, $^2J_{6a,6b}$=11.8 Hz, $^3J_{5,6a}$=4.1 Hz ppm, $^3J_{6aP}$=6.9, H-6a).

$^{31}$P NMR (202 MHz, D$_2$O) δ 3.51 ppm.

Step 6: Preparation of 1,5-Anhydro-2-(3-carbamoylpyridinium)-2,3-dideoxy-6-O-phosphono-D-glucitol 7:

First, 1-(2,4-Dinitrophenyl)-3-carbamoylpyridinium tetrafluoroborate 100 is prepared as follows: 58.6 g Dinitrochlorobenzene is melted under nitrogen and then 29.32 g nicotinamide is added to the melt. It is heated for 2.5 h at 110° C. 500 ml of a 3:2 (v/v) ethanol/water mixture is added through a reflux cooler and reflux boiled until a solution is formed. After stirring overnight at room temperature, 150 ml 50% ethanol/water and 100 ml water are added, transferred to a separating funnel and washed three times with 500 ml chloroform each time. 300 ml and 50 g active carbon is added to the separated aqueous phase which is stirred for 1 h at room temperature and then filtered over a Seitz K700 deep bed filter. The filtrate is concentrated on a rotary evaporator in a vacuum to about 100 ml during which the bath temperature must not exceed 20° C. It is diluted with 300 ml water and 70 g sodium tetrafluoroborate is added while stirring at room temperature. The precipitate is recrystallized from methanol/water. The crystallisate is filtered with a small amount of acetone and then washed with diethyl ether and dried for 24 h in a high vacuum at 40° C.

Yield 100 21.1 g (23%), TLC (Merck, silica gel 60 F-254; butanol/glacial acetic acid/water 5:2:3, R$_f$=0.56.

Next, a solution of 100 (0.148 g, 0.46 mol) in 1.5 H$_2$O is added dropwise during 5 h to a solution of 6 (0.100 g, 0.40 mmol) in 6 ml water and 4 ml methanol while stirring. It is stirred for 4 days at 40° C. During this time 0.3 ml of a 0.5 M aqueous triethylammonium bicarbonate (TEAB) solution is added. The course of the reaction is monitored using TLC. AS soon as no more starting amine is seen, TEAB is added and it is cooled to 0° C. The precipitate is separated by centrifugation. The solvent is removed from the supernatant by distillation on a rotary evaporator. It is prepurified by column chromatography on DEAE Whatman DE-52 cellulose (21 mm×14 cm) using 0.01 M TEAB as the eluant. The main purification is by HPLC on DEAE SEPHADEX™ A-25 cellulose (18 mm×24 cm), equilibrated with 0.01 M TEAB and it is eluted with a TEAB solution of increasing concentration (0.01→0.5 M). The solvent is removed from the combined product fractions by vacuum distillation on a rotary evaporator. The residue id dissolved in 100 ml water and lyophilized. This procedure is repeated three times.

Yield 7 (0.083 g, 59%) yellow solidified oil, R$_f$0.15 (i-PrOH/25%—NH$_4$OH$_{aq}$/H$_2$O 6/4/1). +ESI MS: m/z 333.1 [M$^+$]; −ESI MS: 331.4 [M$^+$−2H]$^−$, $^1$H NMR (200 MHz, D$_2$O) δ 2.40 (ddd, $^2J_{3'ax,3'eq}$=15 Hz, $^3J_{3'ax,4}$=12 Hz, $^3J_{2',3'ax}$=5 Hz, 1H, H-3'ax), 2.66 (dm, $^2J_{3'ax,3'eq}$=15 Hz, $^3J_{3'eq,4}$=5 Hz, 1H, H-3'eq), 3.66 (dm, $^3J_{4',5}$=9 Hz, 1H, H-5'), 3.95 (ddd, $^3J_{3'ax,4'}$=12 Hz, $^3J_{4',5}$=9 Hz, $^3J_{3'eq,4}$=5 Hz, 1H, H-4'), 4.16 (m, 2H, H-6'), 4.26 (dd, $^2J_{1'ax,1'eq}$=14 Hz, $^3J_{1'ax,2}$=3 Hz, 1H, H-1'ax), 4.63 (br.d, $^2J_{1'ax,1'eq}$=14Hz, 1H, H-1'eq), 5.26 (br, 1H, H-2'), 8.27 (dd, $^3J_{4,5}$=8 Hz, $^3J_{5,6}$=6 Hz, 1H, H-5), 8.94 (d, $^3J_{4,5}$=8 Hz, 1H, H-4), 9.39 (d, $^3J_{5,6}$=6 Hz, 1H, H-6), 9.49 ppm (s, 1H, H-2).

Step 7: Preparation of Hexitolnicotinamide adenine dinucleotide lithium salt 8:

First, adenosine-5'-(phosphorus-di-n-butylphosphinothioanhydride) 200 is synthesized according to the relevant literature (Slama, J. T., Radziejewski, C., Oruganti, S., Kaiser, E. T., J. Am. Chem. Soc. (1984), 106, 6778-6785): R$_f$0.9 (i-PrOH/25%—NH$_4$OH$_{aq}$/H$_2$O 6/3/1): $^1$H NMR (500 MHz, D$_2$O) δ 0.78 (m, 6H, CH$_3$), 1.27 (m, 4H, CH$_2$(Bu)), 1.46 (m, 4H, CH$_2$(Bu)), 2.04 (m, 4H, CH$_2$(Bu)), 4.17 (dm, 1H), 4.37 (ddd, 1H), 4.54 (dd, J=5 ml Hz, J=3.7 Hz, 1H), 4.83 (dd, 1H), 6.12 (d, J=5.9 Hz, 1H, H-1'), 8.24 (s, 1H, H-2), 8.46 ppm (s, 1H, H-8). $^{13}$C NMR (125 MHz, D$_2$O) δ 12.91 (CH$_3$), 12.94 (CH$_3$), 23.0 (MeCH$_2$), 24.2 (EtCH$_2$), 33.76 (d, $^1J_{CP}$=68.4 Hz, CP), 33.83 (d, $^1J_{CP}$=68.4 Hz, CP), 65.68 (d, $^2J_{CP}$=5.8 Hz, C-5'), 70.68 (C-3'), 74.13 (C-2'), 83.91 (d, $^3J_{CP}$=9.8 Hz, C-4'), 87.15 (C-1'), 118.84 (C-5), 140.06 (C-8), 149.41 (C-4), 155.86 (C-2), 160.44 ppm (C-6).

$^{31}$P NMR (202 MHz, D$_2$O) δ −9.17 (d, $^2J_{PP}$=34.2 Hz, P=O), 103.9 (d, $^2J_{PP}$=34.2 Hz, P=S).

Accordingly, di-n-butylphosphinothioyl bromide and tetra-n-butyldiphospine disulfide are synthesized according to the relevant literature (Furusawa, K., Sekine, M., Hata, T., J. Chem. Soc., Perkin Trans 1(1976), 1711-1716; Kuchen, W., Buchwald, H., Strolenerg, K., Metten, J., Ann (1962), 652, 28-35).

Next, the nucleotide 7 (0.067 g, 0.2 mol) and 200 (0.211 g, 0.4 mol) are stirred under argon in a mixture of 1 ml dry amine-free DMF and 3 ml pyridine (freshly distilled over BaO). The solvents are removed by distillation in a vacuum. The dissolving and distillation procedure is repeated three times. The residue is then dissolved in a mixture of 2.4 ml absolute DMF and 3 ml absolute pyridine. Silver nitrate (0.274 g, 1.61 mmol) is added all at once in the absence of light and under argon. 15 ml water is added after 40 h stirring at room temperature and H$_2$S is briefly passed in. The silver sulfide precipitate is removed by filtration over celite. The filtrate is washed three times with 5 ml chloroform each time. The solvent is removed from the aqueous phase extract by vacuum distillation on a rotary evaporator. The product is purified by three chromatographies.

1) DEAE SEPHADEX™ A-25 cellulose (18 mm×24 cm), equilibrated with 0.01 M TEAB, elution with TEAB solution (0.01→0.5 M). The solvent is removed from the combined product fraction by vacuum distillation on a rotary evaporator. The residue is dissolved in 100 ml water and lyophilized. This procedure is repeated three times.

2) DEAE Whatman DE-52 cellulose (18 mm×25 cm) pre-equilibrated with water, elution with aqueous formic acid (0→0.3 M). The solvent is removed from the combined product fractions by vacuum distillation on a rotary evaporator. The residue is dissolved in 100 ml water and lyophilized. This procedure is repeated twice. The solution is adjusted to pH 6 with 0.1 M LiOH.

3) SEPHADEX™ LH-20 cellulose (18 mm×31 cm) with water as the eluant. The solvent is removed from the combined product fractions by vacuum distillation on a rotary evaporator. The residue is dissolved in 100 ml water and lyophilized. This procedure is repeated twice.

Yield 8 (0.026 g, 19%) colourless powder, R$_f$0.5 (i-PrOH/25%—NH$_4$OH$_{aq}$/H$_2$O 6/4/1). Exact theoretical mass for C$_{22}$H$_{28}$N$_7$O$_{13}$P$_2$ [M$^+$−2H] 660,1220; found 660,1229 UV(H$_2$O): λ$_{max}$ 259 nm. $^1$H NMR (500 MHz, D$_2$O) δ 2.37 (ddd, $^2J_{3'ax,3'eq}$=15.0 Hz, $^3J_{3'ax,4'}$=11.5 Hz, $^3J_{2',3'ax}$=5.2 Hz, 1H, NH-3'ax), 2.62 (m, $^2J_{3'ax,3'eq}$=15.0 Hz, $^3J_{2',3'eq}$=2.8 Hz, $^2J_{3'eq,4}$=4.8 Hz, $^4J_{1'eq,3'eq}$=2.8 Hz, 1H, NH-3'eq), 3.66 (m, $^3J_{4',5}$=9.2 Hz, $^3J_{5',6'a}$=3.1 Hz, $^3J_{5',6'b}$=3.1 Hz, 1H, NH-5'), 3.95 (ddd, $^3J_{3'ax,4'}$=11.5 Hz, $^3J_{4',5}$=9.2 Hz, $^3J_{3'eq,4'}$=4.8 Hz, 1H, NH-4'), 4.22 (dd, $^2J_{1'ax,1'eq}$=14.4 Hz, $^3J_{1'ax,2'}$=3.1 Hz, 1H, NH-1'ax), 4.24 (m, $^2J_{5'a,5'b}$=12.1 Hz, $^3J_{4',5'a}$=3.1 Hz, 1H, AH-5'a), 4.27 (m $^3J_{5',6'}$=3.1 Hz, 2H, NH-6'), 4.28 (m, $^2J_{5'a,5'b}$=12.1 Hz, $^3J_{4',5'b}$=3.1 Hz, 1H,AH 5'b), 4.40 (m, $^3J_{4',5'a}$=3.1Hz, $^3J_{4',5'b}$=3.1 Hz, $^4J_{4'P}$=1.9 Hz, 1H, AH-4'), 4.53

(dd, $^3J_{2',3'}$=4.7 Hz, $^2J_{3',4'}$=3.1 Hz, 1H, AH-3'), 4.57 (ddd, $^2J_{1'ax,1'eq}$=14.4 Hz, $^3J_{1'eq,2'}$=2.6 Hz, $^4J_{1'eq,3'eq}$=2.8 Hz, 1H, NH-1'eq), 4.74 (t, $^3J_{1',2}$=3.1 Hz, $^3J_{2',3'}$=3.1 Hz, 1H, AH-2'), 5.20 (m, $^3J_{2',3'ax}$=5.1 Hz, $^3J_{2',3'eq}$=2.8 Hz, $^3J_{1'ax,2'}$=3.1 Hz, $^3J_{1'eq,2'}$=2.6 Hz, 1H, NH-2'), 6.14 (d,$^3J_{1',2}$,5.4 Hz, 1H, AH-1'), 8.25 (dd, $^3J_{4,5}$=8.3 Hz, $^3J_{5,6}$=6.1 Hz, 1H, NH-5), 8.40 (s, 1H, AH-2), 8.60 (s, 1H, AH-8), 8.89 (dd, $^3J_{4,5}$=8.3 Hz, $^4J_{2,4}$=1.5 Hz, 1H, NH-4), 9.37 (d, $^3J_{5,6}$=6.1 Hz, $^4J_{2,6}$=1.5 Hz, 1H, NH-6), 9.45 ppm (t, $^4J_{2,4}$=1.5 Hz, 1H, NH-2).

$^{13}$C NMR (125 MHz, D$_2$O) δ 38.39 (NC-3'), 62.59 (NC-4'), 67.45 (dd, $^2J_{6'P}$=4.9 Hz, $^4J_{6'P}$=2.8 Hz, NC-6'), 67.86 (dd, $^2J_{5'P}$=3.7 Hz, $^4J_{5'P}$=2.8 Hz, AC-5'), 69.59 (NC-2'), 69.78 (NC-1'), 73.02 (AC-3'), 77.37 (AC-2'), 83.22 (d, $^3J_{5'P}$=7.9 Hz, NC-5'), 86.89 (d, $^3J_{4'P}$=8.7 Hz, AC-4'), 90.49 (AC-1'), 121.20 (AC-5), 131.48 (NC-5), 136.76 (NC-3) 144.73 (AC-8), 146.72 (NC-2), 147.04 (NC-4), 148.73 (NC-6), 149.22 (AC-4), 151.15 (AC-2), 153.44 (AC-6), 168.50 ppm (CONH$_2$).

$^{31}$P NMR (202 MHz, D$_2$O), δ −10.70 (d, $^2J_{PP}$=20.5 Hz, 1P, AP), −10.31 ppm (d, $^2J_{PP}$=20.5 Hz, 1P, NP).

Synthesis Scheme 2

Figure 2:
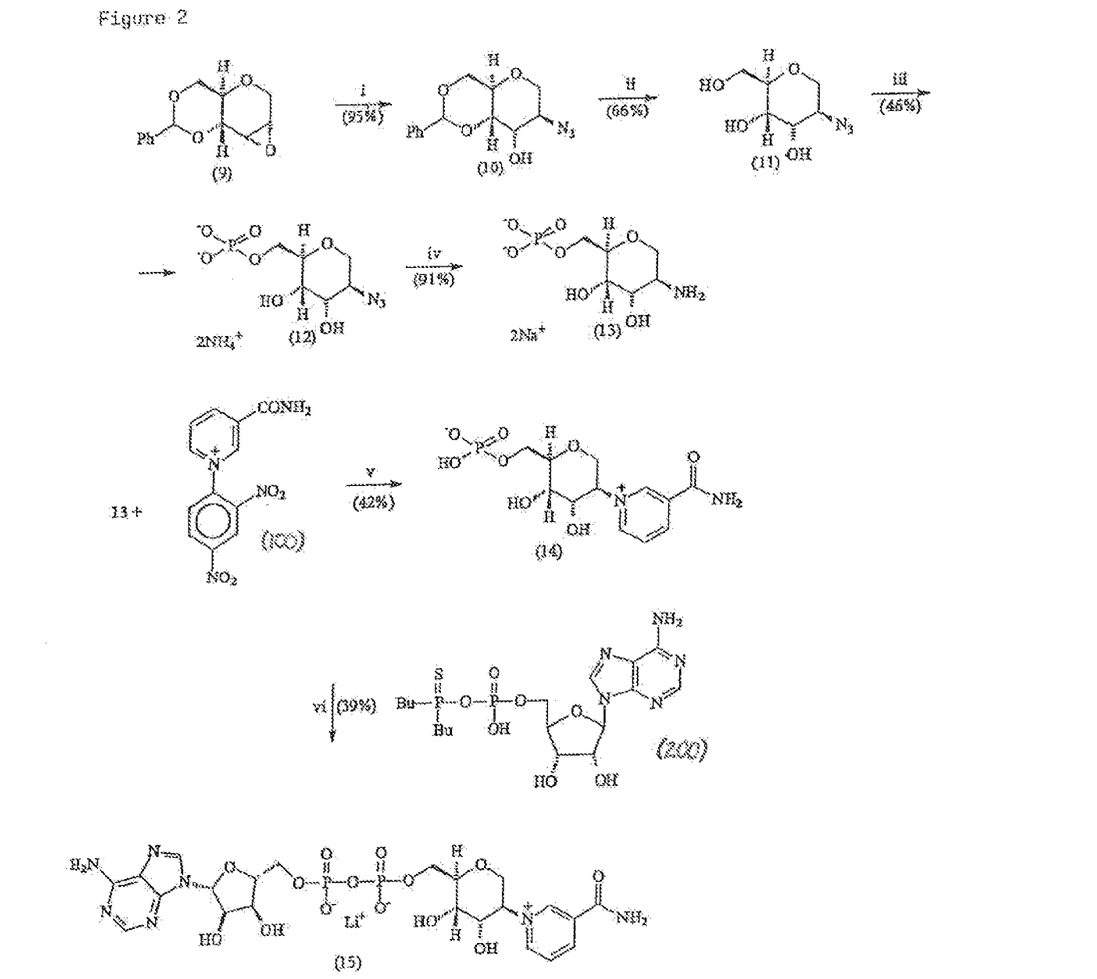
FIG. 2 is a scheme for the preparation of altritol nicotinamide adenine dinucleotide, lithium salt.

Referring now to FIG. 2, an illustrative synthesis scheme is provided for preparation of altritolnicotinamine adenine dinucleotide lithium salt 15 in a series of steps in which numbers refer to like-numbered molecular diagrams in FIG. 2.

Step 1: Preparation of 1,5-anhydro-2-azido-4,6-O-benzylidene-2-deoxy-D-altritol 10:

Sodium azide (1.500 g, 23.07 mmol) and ammonium chloride (1.500 g, 28.04 mmol) are added to a solution of 1,5:2,3-anhydro-4,6-O-benzylidene-D-allitol 9 (Allart B. et al, *Tetrahedron*, 1999, 55, 6527-6546) (1.000 g, 4.27 mmol) in a mixture of 2-methoxyethanol and water 5:1 (240 ml). The mixture is stirred for 18 h under nitrogen at 100° C. After cooling to room temperature the solvent is removed by vacuum distillation on a rotary evaporator. The residue is digested three times with 100 ml warm CHCl$_3$ and then with CH$_2$Cl$_2$ (100 ml). The combined extracts are filtered over a short silica gel column. The solvent is removed by vacuum distillation on a rotary evaporator.

Yield 10 (1.126 g, 95%) pale yellow oil. R$_f$ 0.7 (CH$_2$Cl$_2$/MeOH 98/2). +ESI MS: m/z 278.0 [M+H]$^+$, m/z 300.0 [M+Na]$^+$. $^1$H NMR (200 MHz, CDCl$_3$) δ 2.46 (d, $^3$J=1.5 Hz, 1H, OH), 3.68-3.94 (m, 5H), 4.05 (dd, J=13 Hz, J=2 Hz, 1H), 4.13 (br.s, 1H), 4.32 (m, 1H), 5.65 (s, 1H, PhCH), 7.35-7.55 ppm (m, 5H, aromatic H).

Step 2: Preparation of 1,5-anhydro-2-azido-2-deoxy-D-altritol 11:

A solution of 10 (1.116 g, 4.02 mmol) in 180 ml 80% glacial acetic acid is stirred for 2 h at 95° C. It is stirred in water after evaporation on a rotary evaporator and again evaporated. It is then stirred with toluene and again evaporated. The residue is purified by column chromatography (30-90% EtOAc in hexane). The solvent is removed from the combined product fractions by vacuum distillation on a rotary evaporator. The residue is washed with CHCl$_3$ and dried in vacuum over P$_2$O$_5$.

Yield 11 0.505 g (66%), R$_f$ 0.1 (hexane/EtOAc 1:2) $^1$H NMR (500 MHz, DMSO-d$_6$) δ 3.38-3.45 (m, 3H, H-4, H-5, H-6a), 3.62 (overl. m, 1H, H-6b), 3.64 (overl. m, Δv$_{1/2}$=6 Hz, 1H$_{eq}$, H-2), 3.656 (d, $^2J_{1ax,1eq}$12.2 Hz, 1H, H-1ax), 3.722 (brs, Δv$_{1/2}$=10 Hz, 1H$_{eq}$, H-3), 3.748 (dd, $^2J_{1eq,1ax}$=12.2 Hz, $^3J_{1eq,2}$=1.5 Hz, 1H, H-1eq), 4.457 (brt, 1H, 6-OH), 4.690 (d, J$_{4,OH}$=4.6 Hz, 1H, 4-OH), 5.214 ppm (d, J$_{3,OH}$=4.1 Hz, 1H, 3-OH). $^{13}$C NMR (125 MHz, DMSO-d$_6$), δ 61.15 (CH, C-2), 61.45 (CH$_2$, C-6), 63.05 (CH$_2$, C-1), 65.8 (CH, C-4), 68.21 (CH, C-3), 77.21 ppm (CH, C-5), Step 3: Preparation of 1,5-anhydro-2-azido-2-deoxy-6-O-phosphono-D-altritol diammonium salt 12:

Phosphate 12 is prepared similarly to phosphate 5 starting from azide 11 (0.503 g, 2.66 mmol). Coarse purification by column chromatography and silica gel (0.35% ammonia (20% aqueous solution in i-PrOH) pale yellow oil 12 (0.353 g, 46%). R$_f$ 0.4 (i-PrOH/25%-NH$_4$OH$_{aq}$/H$_2$O 6/4/1). This product is used without further purification.

Step 4: Preparation of 1,5-anhydro-2-amino-2-deoxy-6-O-phosphono-D-altritol disodium salt 13:

25 ml methanol and Adam's catalyst (PtO$_2$.H$_2$O, 0.068 g, 0.28 mmol) are added to a solution of the azide 12 (0.353 g, 1.31 mmol) dissolved in 15 ml water. The mixture is shaken for 85 h in a Parr hydrogenation apparatus (30 psi). The catalyst is removed by filtration and the solvent is removed from the filtrate by distillation on a rotary evaporator under vacuum. The residue is dissolved in water and applied to a Dowex 50WX4-400 (Na$^+$) ion exchange column and eluted with water. The solvent is removed from the combined product fractions by distillation on a rotary evaporator under vacuum. The residue is dried in a vacuum over P$_2$O$_5$.

Yield 13 (0.342 g, 91%) pale yellow amorphous powder. R$_f$ 0.25 (i-PrOH/25% —NH$_4$OH$_{aq}$/H$_2$O 6/4/1). $^1$H NMR (500 MHz, D$_2$O) δ 3.489 (m, 1H, H-2), 3.725 (dt, $^3J_{5,4}$=9.1 Hz, $^3J_{5,6a}$=$^3J_{5,6b}$=3.4 Hz, 1H, H-5), 3.821 (d, $^2J_{1ax,1eq}$=13.2 Hz, 1H, H-1ax), 3.863 (dd, $^3J_{4,5}$=9.1 Hz, $^3J_{4,3}$=3.2 Hz, 1H, H-4), 3.938 (dd, J$_{6,5}$=3.4 Hz, J$_{6,P}$=6.0 Hz, 2H, H-6), 3.967 (dd, $^2J_{1eq,1ax}$=13.2 Hz, $^3J_{1eq,2}$=1.7 Hz, 1H, H-1eq), 4.197 ppm (t, $^3J_{3,2}$=$^3J_{3,4}$=3.2 Hz, 1H, H-3). $^{13}$C NMR (125 MHz, D$_2$O) δ 54.02 (CH, C-2), 65.49 (CH$_2$, C-6), 66.05 (CH$_2$, C-1), 66.11 (CH, C-4), 69.07 (CH, C-3), 78.69 ppm (d, $^3J_{5,P}$=7.3 Hz, CH, C-5).

$^{31}$P NMR (202 MHz, D$_2$O) δ 3.921 ppm.

Step 5: Preparation of 1,5-anhydro-2-(3-carbamoylpyridinium)-2-deoxy-6-O-phosphono-D-altritol 14:

This is prepared in 42% yield similarly to preparation of 7 in Synthesis Scheme 1, by starting from the amine 13 (0.100 g, 0.35 mmol, solution in 4 ml MeOH and 5 ml water), Zincke Cl salt 100 (0.201 g, 0.62 mmol, solution in 2.1 in H$_2$O) and 0.6 ml aqueous 0.5 M TEAB solution.

R$_f$ 0.15 (i-PrOH/25% —NH$_4$—OH$_{aq}$/H$_2$O 6/4/1). $^1$H NMR (200 MHz, D$_2$O) δ 4.02-4.23 (m, 4H), 4.40 (dd, $^2J_{1'ax,1'eq}$=13 Hz, $^3J_{1'ax,2'}$=4 Hz, 1H, H-1'ax), 4.54 (dd, $^2J_{1'ax,1'eq}$=13 Hz, $^3J_{1'eq,2'}$=4 Hz, 1H, H-1'eq), 4.60 (dd, $^3J_{2',3'}$=6.5 Hz, $^3J_{3',4'}$=2 Hz, 1H, H-3'), 5.04 (dt, $^3J_{1'ax,2'}$=4 Hz, $^3J_{1'eq,2'}$=4 Hz, $^3J_{2',3'}$=6.5 Hz, 1H, H-2'), 8.30 (dd, $^3J_{4,5}$=8 Hz, $^3J_{5,6}$=7 Hz, 1H, H-5), 8.99 (d, $^3J_{4,5}$=8 Hz, 1H, H-4), 9.37 (d, $^3J_{5,6}$=7 Hz, 1H, H-6), 9.51 ppm (s, 1H, H-2).

Step 6: Preparation of altritolnicotinamine adenine dinucleotide lithium salt 15:

The nucleotide 14 (0.051, 0.15 mmol) is stirred under argon in a mixture of 2.5 ml dry formamide (pA grade) and 1 ml pyridine (freshly distilled over BaO). The solvents are removed in a vacuum by distillation. The dissolving/distillation procedure is repeated three times. Adenosine-5'-(phosphorus-di-n-butyl-phosphinothio-anhydride) (0.155 g, 0.30 mmol) is added and the mixture is coevaporated three times with absolute pyridine. The residue is then dissolved in 2.0 ml absolute pyridine. Silver nitrate (0.200 g, 1.18 mmol, dried for 2 h at 120° C.) is added all at once in the absence of light and under argon. 15 ml water is added after 65 h stirring at room temperature and then the subsequent procedure is as described for 8 using a solution of 200.

Yield lithium salt 15 (0.039 g, 39%) colourless powder, $R_f$ 0.4 (i-PrOH/25% —$NH_4OH_{aq}$/$H_2O$ 6/4/1). Theoretical mass for $C_{22}H_{28}N_7O_{14}P_2$ [M+−2H] 676.1169. Found 676.1147, −ESI MS: m/z 6.76 [M$^+$−2H]$^-$, m/z 6.98 [M$^+$−3H+Na]$^-$; +ESI MS: m/z 678 [M$^+$], m/z 700 [M$^+$−H+Na]. UV($H_2O$): $\lambda_{max}$259 nm.

$^1$H NMR (500 MHz, $D_2O$) δ 4.10 (m, 1H, NH-5'), 4.10 (m, $^3J_{3',4'}$=5.8 Hz, 1H, NH-4'), 4.24 (m, $^2J_{5'a,5'b}$=11.7 Hz, $^3J_{4',5'a}$=3.3 Hz, 1H, AH-5'a), 4.27 (m, $^2J_{5'a,5'b}$=11.7 Hz, $^3J_{4',5'b}$=2.6 Hz, 1H, AH-5'b), 4.29 (m, 2H, NH-6'), 4.36 (dd, $^2J_{1'ax,1'eq}$=13.2 Hz, $^3J_{1'ax,2'}$=4.1 Hz, 1H, NH-1'ax), 4.41 (m, $^3J_{3',4'}$=3.2 Hz, $^3J_{4',5a}$=3.3 Hz, $^3J_{4',5'b}$=2.6 Hz, 1H, AH-4'), 4.46 (dd, $^2J_{1'ax,1'eq}$=13.2 Hz, $^3J_{1'eq,2'}$=4.6 Hz, 1H, NH-1'eq), 4.53 (dd, $^3J_{3',4'}$=5.8 Hz, $^3J_{2',3'}$2.7 Hz, 1H, NH-3'), 4.53 (dd, $^3J_{2',3'}$=5.1 Hz, $^3J_{3',4'}$=3.2 Hz, 1H, AH-3'), 4.77 (dd, $^3J_{1',2'}$5.7 Hz, $^3J_{2',3'}$=5.1 Hz, 1H, AH-2'), 5.02 (ddd, $^3J_{1'ax,2'}$=4.1 Hz, $^3J_{1'eq,2'}$=4.6 Hz, $^3J_{2',3'eq}$=2.7 Hz, 1H, NH-2'), 6.13 (d, $^3J_{1',2'}$=5.7 Hz, 1H, AH-1'), 8.25 (dd, $^3J_{4,5}$=8.3 Hz, $^3J_{5,6}$=6.0 Hz, 1H, NH-5), 8.31 (s, 1H, AH-2), 8.53 (s, 1H, AH-8), 8.91 (dd, $^3J_{4,5}$=8.3 Hz, $^4J_{2,4}$=1.5 Hz, 1H, NH-4), 9.30 (dd, $^4J_{5,6}$=6.0 Hz, 4$J_{2,6}$=1.5 Hz, 1H, NH-6), 9.44 (t, $^4J_{2,4}$=1.5 Hz, $^4J_{2,6}$=1.5 Hz, 1H, NH-2). $^{13}$C NMR (125 MHz, $D_2O$) δ 66.40 (NC-1'), 67.66 (dd, $^2J_{6'P}$=5.0 Hz, NC-6'), 67.86 (d, $^2J_{5'P}$=6.4 Hz, AC-5'), 68.00 (NC-4'), 72.12 (NC-3'), 73.08 (NC-2'), 73.17 (AC-3'), 77.07 (AC-2'), 79.41 (d, $^3J_{5'P}$=6.9 Hz, NC-5'), 86.67 (d, $^3J_{4'P}$=7.5 Hz, AC-4'), 89.91 (AC-1'), 121.23 (AC-5), 131.63 (NC-5), 136.80 (NC-3), 144.26 (AC-8), 146.75 (NC-2), 147.71 (NC-4), 148.95 (NC-6), 151.16 (AC-4), 151.46 (AC-2), 153.35 (AC-6), 165.67 ppm ($CONH_2$). $^{31}$P NMR (202 MHz, $D_2O$) δ −10.68 ppm.

Synthesis Scheme 3

Figure 3:
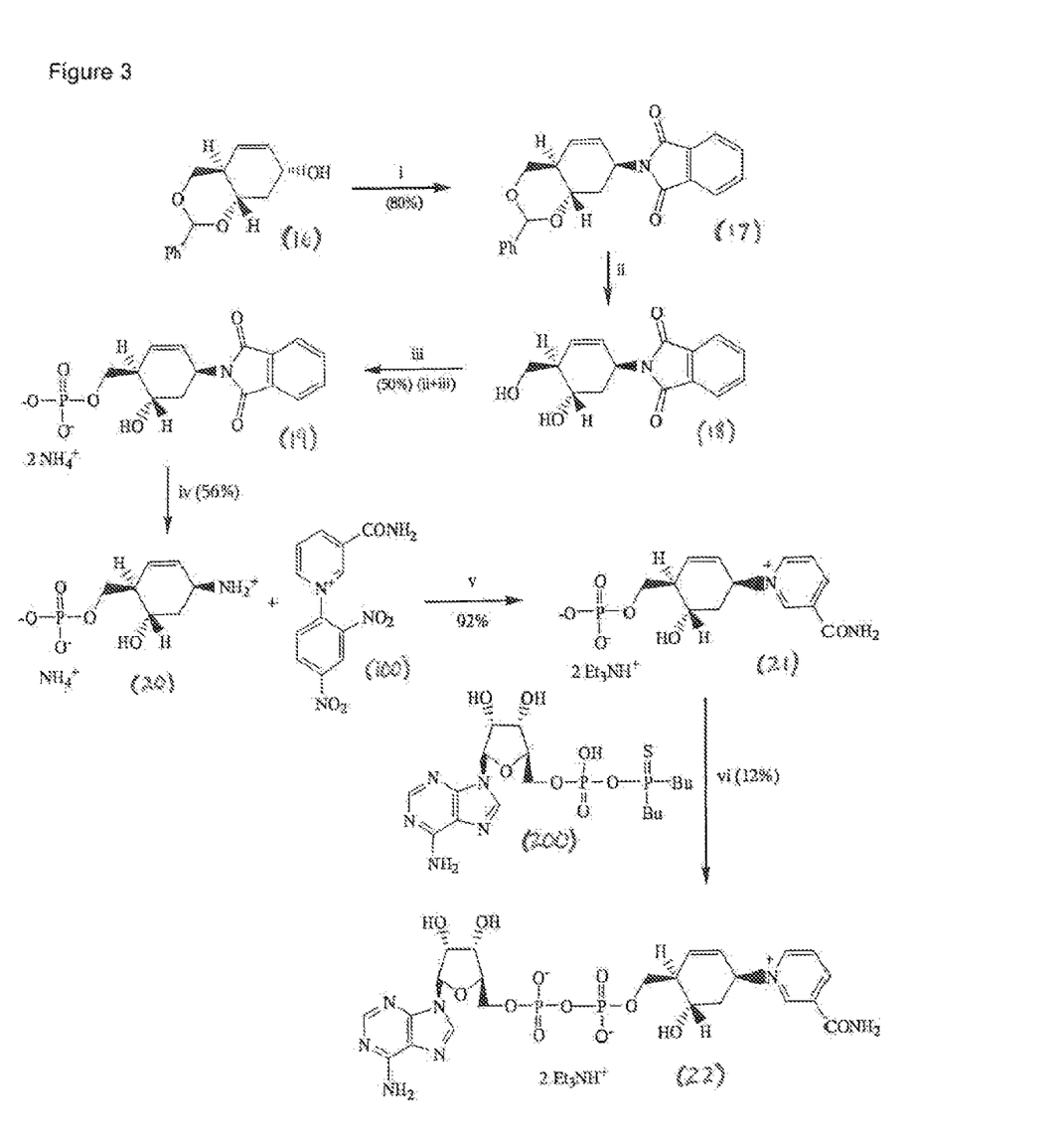
FIG. 3 is a scheme for the preparation of cyclohexene nicotinamide adenine nucleotide.

Referring now to FIG. 3, an illustrative synthesis scheme is provided for preparation of cyclohexenylnicotinamide adenine dinucleotide triethylammonium salt 22 in a series of steps in which numbers refer to like-numbered molecular diagrams in FIG. 3.

Step 1: Preparation of (1S, 4R, 5S)-N-(5-hydroxy-4-hydroxymethyl-5,7-O-benzylidene-2-cyclohexen-1-yl)phthalimide 17:

A solution of DIAD (5.3 ml, 25.52 mmol) in absolute THF (50 ml) is added slowly under nitrogen to a suspension of triphenylphosphine (7 g, 26.68 mmol), 16)(Wang J. Et. al., *J. Org. Chem.*, 2001, 66, 8478-8482; Gu P. et. al., *Tetrahedron*, 2004, 60, 2111-2123), (4.2 g, 18.08 mmol) and phthalimide (4 g, 27.18 mmol) in dry THF (170 ml) while stirring at room temperature. After stirring for 1 hr, it is rotary evaporated. The residue is purified by column chromatography (EtOAc/hexane 2/8). The solvent is removed from the combined product fractions by distillation on a rotary evaporator under vacuum.

Yield 17 5.23 g, (80% colourless solid. $^1$H NMR (CDCl$_3$, 500 MHz) δ 2.14-2.18 (1H, m $J_{6,6'}$=13.9 Hz, $J_{6,1}$=4.1 Hz, H6), 2.26-2.32 (1H, m, H6'), 2.51 (1H, m, H4), 3.86 (1H, m, $^2J$=11.1 Hz, H7), 4.35-4.38 (1H, dd, J=10.7 Hz, J=4.4 Hz, H7'), 4.44-4.49 (1H, m, H5), 5.11 (1H, m, H1), 5.65-5.7 (3H, m, H2, H3, CHφ), 7.34-7.3 (9H, H arom.)

$C_{22}H_{19}NO_4$ (361): ESI: 362 (M+H)$^+$, 384 (M+Na)$^+$.

Step 2: Preparation of (1S, 4R, 5S)-N-(5-hydroxy-4-hydroxymethyl-2-cyclohexen-1-yl)phthalimide 18:

A suspension of 17 (1.116 g, 4.02 mmol) in 80 ml 80% glacial acetic acid is stirred at 95° C. until a clear solution is formed. After evaporation on a rotary evaporator it is stirred in water and again evaporated. Then it is stirred with toluene and again evaporated. The residue is purified by column chromatography (EtOAc/hexane from 1/1 to 7/3). The solvent is removed from the combined product fractions by distillation under vacuum on a rotary evaporator.

Yield 18 3.4 g, (90%). $^1$H-NMR (DMSO-d6, 500 MHz) δ 1.76 (1H, m, H4), 2.16 (2, m, H6), 3.41 (2H, m, H7+H7'), 4.04 (1H, m, H-5), 4.69 (1H, 7-OH), 4.76 (1H, d, J=3.5 Hz, 3-OH), 4.94 (1H, m, H1), 5.63 (1H, m, H3), 5.67 (1H, m, H1), 7.83 (4H, Hpht.) $C_{15}H_{15}NO_4$ (273): ESI 274 (M+H)$^+$, 296 (M+Na)$^+$.

Step 3: Preparation of (1S, 4R, 5S)-1-amino-4-O-phosphonomethyl-5-hydroxy-2-cyclohexene ammonium salt 20:

Phosphorusoxy chloride (436 µl) is added to trimethyl phosphate (5.5 ml) while stirring under argon at 0° C. After stirring for 15 min at 0° C., 18 (600 mg, 2.19 mmol) is added all at once. After stirring for 3 h, 50 ml cold water is added and it is neutralized dropwise with triethylamine. The mixture is evaporated to dryness under vacuum on a rotary evaporator. The residue is washed with diisopropyl ether and purified by column chromatography on silica gel using iPrOH/NH$_4$OH/H$_2$O (6/3/1) as the eluant. The solvent is removed from the combined product fractions by distillation under vacuum on a rotary evaporator.

Yield 19 as a colourless solid (475 mg, 56).

19 (300 mg, 0.775 mmol) is dissolved in 15 ml EtOH/H$_2$O (1/1) and admixed with hydrazine monohydrate (75 µl, 1.55 mmol). After stirring overnight at 90° C., the solvents are removed by distillation under vacuum on a rotary evaporator. The residue is dissolved in water and washed with ethyl acetate. The solvent is removed from the aqueous phase by distillation under vacuum on a rotary evaporator. The residue is washed with diisopropyl ether and purified by column chromatography on silica gel using iPrOH/NH$_4$OH/H$_2$O (6/3/1) as the eluant. The solvent is removed from the combined product fractions by distillation under vacuum on a rotary evaporator.

Yield 20 (111 mg, 56%). $^1$H-NMR (D$_2$O, 500 MHz) δ 2.026 (ddd, J$_{6,6'}$=13.9 Hz, J$_{6,5}$=6.6 Hz, J$_{6,1}$=3.2 Hz, 1H, H6), 2.50 (ddd, J$_{6,6'}$=13.9 Hz, J$_{6,5}$=8.1 Hz, J$_{6'1}$=5.8 Hz, 1H, H6'), 2.43 (m, 1H, H4), 3.863 (dt, J$_{7,7'}$=10.2 Hz, J$_{7,5}$=J$_{7,P}$=5.6 Hz, 1H, H7), 3.976 (dt, J$_{7,7'}$=10.2 Hz, J$_{7',5'}$=J$_{7'P}$=5.1 Hz, 1H, H7'), 4.031 (m, 1H, H1), 4.148 (ddd, J$_{5,6}$=8.2 Hz, J$_{5,4}$=5.1 Hz, J$_{5,6}$=3.3 Hz, 1H, H5), 5.855 (dt, J$_{3,2}$=10.2 Hz, J$_{3,4}$=J$_{3,1}$=2.5 Hz, 1H, H3), 6.004 ppm (dm, J$_{2,3}$=10.2 Hz, 1H, H2). $^{31}$P-NMR (D$_2$O 202 MHz) δ 1.95 ppm(s). Exact theoretical mass $C_7H_{13}NO_5P$: 222.1477. Found 222.0523.

Step 4: Preparation of (1S, 4S, 5S)-1-(carbamoylpyridine)-4-phosphonomethyl-5-hydroxy-2-cyclohexene triethylammonium salt 21:

20 (0.07 g, 0.26 mmol) is stirred for 30 min at room temperature under nitrogen in a mixture of MeOH (4.5 ml) and dry Hünig base iPr$_2$EtN (0.09 ml, 0.52 mmol). The Zincke BF4 salt (0.1 g, 0.28 mmol) is added all at once. The deep-red mixture is stirred for 5 h at 55° C. and an additional 0.03 g Zincke tetrafluoroborate salt is added and heated for a further 20 h. 50 ml of a TEAB (1M) solution is added and evaporated to dryness on a rotary evaporator under vacuum. The crude product is purified by MPLC on DEAE cellulose. Firstly undesired by-products are eluted with water. Then the elution is continued with a gradient of 0.01 M TEAB to 0.5 M TEAB at flow rate of 1 ml/min. The solvent is removed from the combined product fractions by distillation under a vacuum on a rotary evaporator.

Yield 21 0.09 g (92%): colourless amorphous powder. $^1$H-NMR (D$_2$O, 500 MHz) δ 2.31-2.35 (ddd, $J_{6',6'}$=13.8 Hz, $J_{6',5'}$=6.6 Hz, $J_{6,1}$=3.1 Hz, 1H, H6'), 2.48-2.54 (dm, $J_{6,6'}$=13.8 Hz, 1H, H6'), 2.59 (m, 1H, H4'), 4.05-4.11 (m, 3H, H7', H7'', H5'), 5.67 (m, 1H, H1'), 6.05 (m, 1H, H3'), 6.41 (dm, $J_{2,3}$=11.5 Hz, 1H, H2'), 8.22 (dd, $J_{5,4}$=8 Hz, $J_{5,6}$=6 Hz, 1H, H5), 8.92 (d, $J_{4,5}$=8 Hz, 1H, H4), 9.12 (d, $J_{6,5}$=6.1 Hz, 1H, H6), 9.35 (s, 1H, H2). $^{31}$P-NMR (D$_2$O, 2.02 MHz) δ 1.02 ppm(s). Exact theoretical mass C$_{13}$H$_{16}$N$_2$O$_6$P: 327.2514. Found 327.0739.

Step 5 : Preparation of cyclohexenylnicotinamide adenine dinucleotide triethylammonium salt 22:

9 ml of a 1:1 mixture of DMF/pyridine is added to the mononucleotide 21 (0.095 g, 0.178 mmol) and 200 (0.186 g, 0.356 mmol). The solvent is removed by distillation in a vacuum and it is taken up again in 9 ml of a 1:1 mixture of DMF/pyridine. This procedure is repeated once again. The residue is then thoroughly dried in a high vacuum and then again taken up in 9 ml of a 1:1 mixture of DMF/pyridine. Silver nitrate (0.242 g, 1.424 mmol) is added all at once in the absence of light and under argon. After 15 h stirring at room temperature 30 ml water is added and H$_2$S is briefly passed in . The silver sulfide precipitate is removed by filtration over celite. The filtrate is washed three times with 5 ml chloroform each time. The solvent is removed from the aqueous phase by distillation under vacuum on a rotary evaporator. The crude product is purified by MPLC on DEAE cellulose. Firstly undesired by-products are eluted with water. Then the elution is continued with a gradient of 0.01 M TEAB to 0.25 M TEAB at a flow rate of 1 ml/min. The solvent is removed from the combined product fractions by distillation under vacuum on a rotary evaporator.

Yield 22 0.018 g (12%) colourless powder. $^1$H-NMR (D$_2$O, 500 MHz) δ 2.23 (1H, ddd, $J_{NH6'-NH6''}$14 Hz, $J_{NH6'-NH6''}$8.3 Hz, $J_{NH6'-NH1'}$6 Hz, NH6'), 2.39 (1H, ddd, $J_{NH6'-NH6''}$=14.2 Hz, $J_{NH6''-NH1''}$=6.2 Hz, $J_{NH6''-NH5''}$=3.1 Hz, NH5''), 2.48 (1H, m, $J_{NH5'-NH4'}$=5.5 Hz, $J_{NH4'-NH6'}$=4.5 Hz, $J_{NH4'-NH3'}$=3.1 Hz, $J_{NH4'-NH2'}$=2.8 Hz, NH4'), 4.04 (1H, ddd, $J_{NH5'-NH6'}$=8.3 Hz, $J_{NH5'-NH4'}$=5.5 Hz, $J_{NH5'-NH6''}$=3.1 Hz, NH5'), 4.09-4.14 (2H, dAB, $J_{NH7'-NH7''}$=10.6 Hz, $J_{NH7'-NH4'}$=4.5 Hz, $J_{NH7''-NH4'}$=3.8 Hz, NH7'-NH7''), 4.20-4.23 (2H, dAB, $J_{AH5'-AH5''}$=11.9 Hz, $J_{AH5'-AH4'}$=3.1 Hz, $J_{AH5''-AH4'}$=3.5 Hz, AH5'-AH5''), 4.37 (1H, m, $J_{AH4''-AH3'}$=3.2 Hz, $J_{AH4'-AH5'}$=3.1 Hz, $J_{AH4'-AH5''}$=3.5 Hz, AH4'), 4.50 (1H, dd, $J_{AH3'-AH2'}$=5.6 Hz, $J_{AH3'-AH4'}$=3.2 Hz, AH3'), 4.75 (1H, dd, $J_{AH2'-AH1'}$=5.9 Hz, $J_{AH2'-AH3'}$=5.6 Hz, AH2'), 5.57 (1H, m, $J_{NH1'-NH6''}$=6.2 Hz, $J_{NH1'-NH6'}$=6.0 Hz, $J_{NH1'-NH2'}$=2.8 Hz, $J_{NH1'-NH3'}$=1.6 Hz, NH1'), 5.90 (1H, m, $J_{NH2'-NH3'}$=10.2 Hz, $J_{NH2'-NH4'}$=2.8 Hz, $J_{NH2'-NH1'}$=2.8 Hz, NH2'), 6.06 (1 H, d, $J_{AH1'-AH2'}$=5.9 Hz, AH1'), 6.28 (1H, m, $J_{NH3'-NH2'}$=10.2 Hz, $J_{NH3'-NH4'}$=3.1 Hz, $J_{NH3'-NH1'}$=1.6 Hz, NH3'), 8.15 (1H, dd, $J_{NH5-NH4}$=8.1 Hz, $J_{NH5-NH6}$=6.2 Hz, NH5), 8.19 (1H, s, AH8), 8.45 (1H, s, AH2), 8.80 (1H, d, $J_{NH4-NH5}$=8.1 Hz, NH4), 9.00 (1H, d, $J_{NH6-NH5}$=6.2 Hz, NH6), 9.27 ppm (1H, m, $J_{NH2-NH4}$=1.5 Hz, $J_{NH2-NH6}$=1.5 Hz, NH2).

$^{13}$C-NMR (D$_2$O, 125 MHz) δ 38.53 (NC6') 46.10 (NC4', d, $J_{NC4'-NP}$=8.8 Hz), 66.00 (NC5'), 68.01 (NC7', d, $J_{NH7'-NP}$=5.8 Hz), 68.18 (AC5', d, $J_{AC5'-AP}$=4.8 Hz, 69.88 (NC1'), 73.07 (AC3'), 76.75 (AC2'), 86.61 (AC4', d, $J_{AC4'-AP}$=8.7 Hz), 89.50 (AC1'), 121.16 (AC5), 125.08 (NC2'), 131.26 (NC5), 136.53 (NC3), 139.57 (NC3'), 142.54 (AC8), 145.98 (NC2), 147.12 (NC4), 148.04 (NC6), 155.45 (AC2), 158.04 (AC4), 158.08 (AC6), 168.13 ppm (CONH$_2$).

$^{31}$P-NMR (D$_2$O, 202 MHz) δ −10.88 (1P, d, $J_{NP-AP}$=20.4 Hz, NP), −10.57 ppm (1P, d, $J_{NP-AP}$=20.4 Hz, AP).

Theoretical mass C$_{23}$H$_{29}$N$_7$O$_{12}$P$_2$: 657.471. Found: 657.1313.

It is noted that terms like "preferably", "commonly", and "typically" are note utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which quantitative representation may vary from a stated reference without resulting in a change in the basic function of the subject matter at issue.

Having thus described the invention in detail and by reference to specific embodiments thereof, it will be apparent that modification and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A test element for determining an analyte, comprising (i) a nicotinamide coenzyme-dependent enzyme or a substrate for such an enzyme, and (ii) a coenzyme comprising a compound of the following general formula (I) or a salt or a reduced form thereof:

in which
A=adenine or an analog thereof,
T=O or S,
U=OH, SH, BH$_3$—, or BCNH$_2$—,
V=OH or a phosphate group,
W=COOR, CON(R)$_2$, COR, or CSN(R)$_2$, in which R=H or C$_1$-C$_2$-alkyl $X_1$, $X_2$=O, $CH_2$, $CHCH_3$, $C(CH_3)_2$, NH, or $NCH_3$, Y=NH, S, O, or $CH_2$,

Z= a saturated or unsaturated carbocyclic or heterocyclic six-membered ring, and a residue $C(R_4)_2$ bound to the six-membered ring and to $X_2$, where $R_4$=H, F, or $CH_3$, wherein the six-membered ring and the pyrimidine residue are not linked by a glycosidic bond.

2. The test element of claim 1, wherein said test element is configured for the determination of glucose, and said enzyme comprises glucose dehydrogenase.

3. The test element of claim 1, wherein the six membered ring of Z comprises one or more substituents selected from the group consisting of OH, F, Cl and $C_1$-$C_2$ alkyl.

4. The test element of claim 3, wherein the substituent $C_1$-$C_2$ alkyl comprises one or more of a fluorinated, chlorinated or OH-substituted O—$C_1$-$C_2$ alkyl.

5. The test element of claim 1, wherein Z comprises a compound having the general formula (II):

(II)

in which a single or double bond can in each case independently be present between $R_1$ and $R_2$ or between $R_1'$ and $R_2'$, wherein if a single bond is present between $R_1$ and $R_2$ or $R_1'$ and $R_2'$ respectively:

$R_1$, $R_1'$=O, S, $NCH_3$, NH, $C(R_4)_2$, CHOH, or $CHOCH_3$, where $R_1$ or $R_1'$ cannot at the same time be a heteroatom, and $R_2$, $R_2'$=$C(R4)_2$, CHOH, or $CHOCH_3$;

and wherein if a double bond is present between $R_1$ and $R_2$ or $R_1'$ and $R_2'$ respectively:

$R_1$, $R_1'$, $R_2$, $R_2'$=$CR_4$, and $R_4$=H, F, Cl, or $CH_3$; and $R_6$, $R_6'$=CH or $CCH_3$.

6. The test element of claim 1, wherein W=$CONH_2$ or $COCH_3$.

7. The test element of claim 1, wherein the test element is in the form of a test strip configured for electrochemical or optical determination of the analyte.

8. The test element of claim 1, wherein the enzyme comprises a dehydrogenase selected from glucose dehydrogenase, lactate dehydrogenase, malate dehydrogenase, glycerol dehydrogenase, alcohol dehydrogenase, alpha-hydroxybutyrate dehydrogenase, sorbitol dehydrogenase, and amino acid dehydrogenase selected from L-amino acid dehydrogenase.

9. The test element of claim 8 configured for detecting glucose and wherein the enzyme is glucose dehydrogenase.

10. A test element for determining an analyte, comprising a nicotinamide coenzyme dependent enzyme-coenzyme complex comprising the coenzyme of claim 1 in combination with a suitable nicotinamide coenzyme dependent enzyme and in combination with a suitable reaction buffer, and configured to determine one or more analytes selected from the group consisting of glucose, lactic acid, malic acid, glycerol, alcohol, cholesterol, triglycerides, ascorbic acid, cysteine, glutathione, peptides, urea, ammonia, salicylate, pyruvate, 5'-nucleotidase, creatine kinase (CK), lactate dehydrogenase (LDH), and carbon dioxide.

11. A method for detecting an analyte comprising the steps of:

(a) contacting a sample with the test element of claim 1, and (b) detecting the analyte by one of electrochemistry, photometry or fluorometry.

* * * * *